United States Patent
Hawkins et al.

(10) Patent No.: US 8,808,387 B2
(45) Date of Patent: Aug. 19, 2014

(54) PROSTHETIC JOINT

(75) Inventors: Douglas Sherman Hawkins, Morgantown, WV (US); Mari Susan Truman, Warsaw, IN (US)

(73) Assignee: Epic Ortho, LLC, Morgantown, WV (US)

(*) Notice: Subject to any disclaimer, the term of this patent is extended or adjusted under 35 U.S.C. 154(b) by 86 days.

(21) Appl. No.: 13/358,777

(22) Filed: Jan. 26, 2012

(65) Prior Publication Data

US 2013/0197653 A1 Aug. 1, 2013

(51) Int. Cl.
*A61F 2/38* (2006.01)

(52) U.S. Cl.
USPC ............ 623/20.27; 623/20.14; 623/20.21; 623/20.31

(58) Field of Classification Search
USPC .......... 623/20.14, 20.21, 20.22, 20.23, 20.27, 623/20.31
See application file for complete search history.

(56) References Cited

U.S. PATENT DOCUMENTS

| | | | |
|---|---|---|---|
| 4,959,071 A * | 9/1990 | Brown et al. | 623/20.27 |
| 5,133,758 A | 7/1992 | Hollister | |
| 5,326,361 A | 7/1994 | Hollister | |
| 5,522,900 A | 6/1996 | Hollister | |
| 5,549,688 A | 8/1996 | Ries et al. | |
| 5,549,690 A | 8/1996 | Hollister et al. | |
| 6,770,099 B2 | 8/2004 | Andriacchi et al. | |
| 7,326,252 B2 | 2/2008 | Otto et al. | |
| 7,465,320 B1 * | 12/2008 | Kito et al. | 623/20.27 |
| 7,922,770 B2 * | 4/2011 | Tsakonas | 623/20.27 |
| 7,955,394 B2 * | 6/2011 | Hotokebuchi et al. | 623/20.14 |
| 2004/0243244 A1 | 12/2004 | Otto et al. | |
| 2010/0234961 A1 | 9/2010 | Otto et al. | |
| 2013/0190884 A1 * | 7/2013 | Hashida | 623/20.29 |

OTHER PUBLICATIONS

AGC Biomet "Selected Scientific Papers," Proc. of the Intl. Symposium on Current Topics in Knee Arthroplasty, Marbella, Spain (Jun. 13-15, 2007).

Postak et al., "Performance Characteristics of Modular Total Knee Systems," The Mt. Sinai Medical Center, Case Western Reserve University (1991).

Postak et al., "Stability Characteristics of Total Knee Replacements," The Mt. Sinai Medical Center, Case Western Reserve University [date unknown].

Hefzy et al., "Kinematics of the knee joint in deep flexion: a radiographic assessment," Medical Engineering & Physics 20, pp. 302-307 (1998).

(Continued)

*Primary Examiner* — David Isabella
*Assistant Examiner* — Dinah Baria
(74) *Attorney, Agent, or Firm* — Saul Ewing LLP

(57) ABSTRACT

A joint prosthesis includes e.g., a femoral component and a tibial component. The medial and lateral condylar articular surfaces may have substantially uniform and equal radii from full extension to about 90° of flexion. From 90°, the lateral condylar articular surface has a smaller radius than the medial condylar articular surface such that the medial condyle gradually becomes increasingly more proud than the lateral condyle to facilitate internal rotation of the tibia at deep flexion. Also, the tibial articular component may include a post intermediate the medial and lateral compartments that engages a cam on the femoral articular component between the medial and the lateral condylar articular surfaces. The cam and post become congruent at flexion angles of approximately 70° flexion and mate symmetrically during the first 20°-30° of further flexion, and then mate asymmetrically at greater degrees of flexion to force internal rotation of the tibia.

5 Claims, 16 Drawing Sheets

(56) References Cited

OTHER PUBLICATIONS

Journey BCS, Smith & Nephew, Benefits, pp. 1-4, retrieved from the Internet, URL: http://global.smith-nephew.com/us/journey_bcs_23617_4916.htm, retrieved Mar. 1, 2011.

Evolution Medial-Pivot Knee System, Experience Stability [date unknown].

Launch of Journey Bi-Cruciate Stabilized Knee System, Smith & Nephew, pp. 1-5; retrieved from the Internet, URL: http://www.medicalnewstoday.com/articles/41286.php, retrieved Mar. 1, 2011.

Devers et al., J. of Arthroplasty, vol. 26, No. 2, pp. 178-186 (2011).

Komistek et al., J. Arthroplasty, vol. 23, No. 1, pp. 41-50 (2008).

Freeman et al., J. Biomechanics, vol. 38, pp. 197-208 (2005).

* cited by examiner posterior ←——————→ anterior

↓ distal medial ——————————————— lateral medial ←——————→ lateral

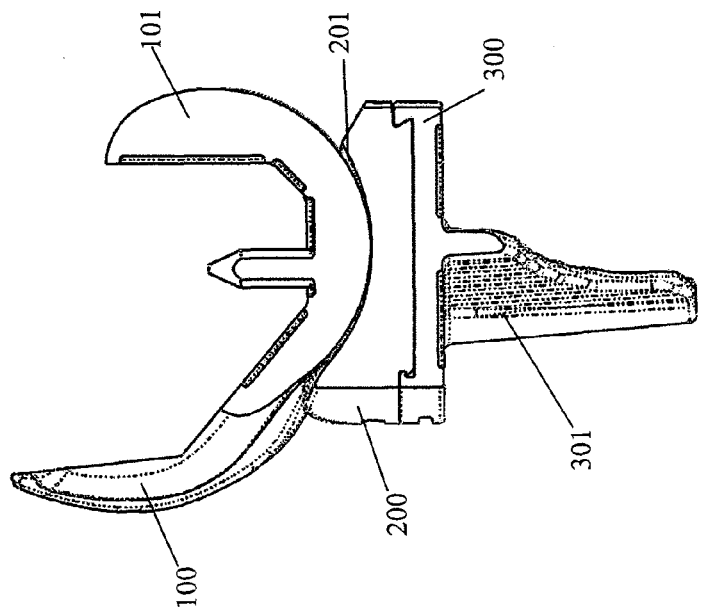
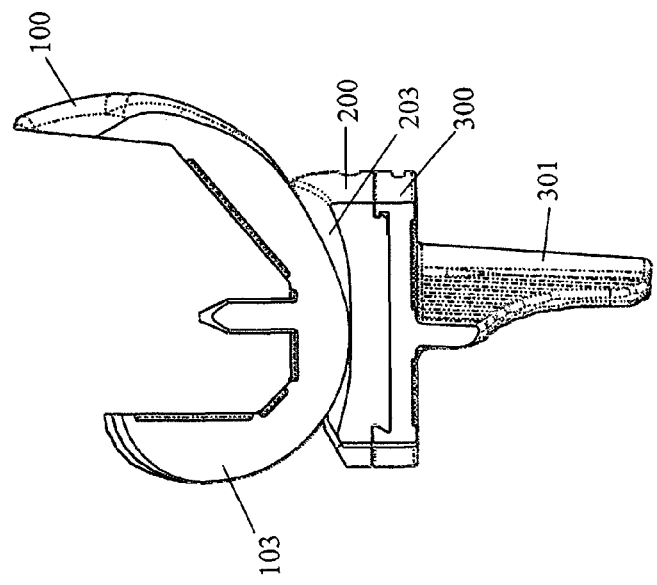

PROSTHETIC JOINT

FIELD OF THE INVENTION

The present invention relates generally to total joint replacement orthopedic prosthetics. More particularly, the invention relates to a total knee replacement (TKR) implant for use total knee arthroplasty ("TKA").

BACKGROUND OF THE INVENTION

Disease and trauma affecting the articular surfaces of a joint, such as the knee joint, often are treated by surgically replacing the articular surfaces of the bones that meet at the joint, such as the femur and tibia of the knee joint, with prosthetic femoral and tibial implants, referred to as total knee replacements ("TKR").

In total knee replacement (TKR) surgery, a surgeon typically will surgically resect the distal end of the patient's femur (typically at a base angle orthogonal to the mechanical axis of the leg as measured in an A-P X-ray) and replace it with a femoral articular component.

The femoral articular component may be mounted directly to the resected end of the femur or, for added strength and bonding, may be mounted on a femoral stem component that is inserted into an intramedullary canal drilled into the femur.

The femoral articular component will commonly comprise a medial condylar articular surface and a lateral condylar articular surface separated by at least a partially open space, thereby simulating the distal end of a natural femur. The medial and lateral condylar articular surfaces of the femoral articular component replace and serve the function of the medial and lateral condyles of the natural knee.

The surgeon also will surgically resect the proximal end of the tibia (also, typically perpendicular to the mechanical axis of the leg as measured in an A-P X-ray, even though the plateau at the proximal end of a natural tibia typically has is slightly varus angulated) and replace it with a tibial articular component comprising a tibial articular surface. Usually, the tibial implant includes a tibial stem component that extends at an angle to a tibial plateau. The stem will extend into a surgically formed opening in the patient's intramedullary canal of the tibia. The stem component may be formed of titanium or cobalt chromium alloys compatible with the tibial tray implant or another biocompatible metal. A plastic or polymeric (often ultra high molecular weight polyethylene) insert (or bearing) articular component is placed atop the plateau at the proximal end of the stem component and comprises the tibial articular surfaces upon which the condylar articular surfaces of the femoral articular component will ride.

The tibial insert commonly will comprise medial and lateral compartments comprising medial and lateral articular surfaces that mate with the medial and lateral condyles on the femoral articular component, respectively. The medial and lateral articular surfaces on the tibial articular component replace and serve the function of the medial and lateral menisci of the natural knee.

One or both of the femoral and tibial articular surfaces typically are made of biocompatible, low friction, hard material, such as cobalt chromuim or a polymer, such as a high molecular weight polyethylene.

In a natural knee, the relative movement of the femur, tibia, and patella (the knee cap) is a complex combination of flexion-extension, translation, and rotational movements in all six degrees of freedom and is difficult to emulate with a prosthesis. For instance, in a natural knee, the condyles of the femur translate relative to the tibial bone as well as rotate. The overall translation is much greater in the lateral compartment than in the medial compartment (e.g., from 0 to 120 degrees of flexion, the tibio-femoral contact point moves on average about 20 mm on the lateral side and about 12 mm on the medial side. (See Walker P S, Heller Y, Yildirim G, Immerman I.: *Reference axes for comparing the motion of knee replacements with the anatomic knee. Knee.* 2011 October; 18(5): 312-6. Epub 2010 Aug. 17.)) Intracapsular anatomical structures such as the ACL (Anterior Cruciate Ligament), PCL (Posterior Cruciate Ligament), menisci, the bone anatomy, and the muscles acting on the knee joint influence a phenomenon called the screw home mechanism. Particularly, the two rounded ends (condyles) of the femur have different radii. During knee extension, the tibia glides anteriorly on the femur. Through the last 20 degrees of knee extension, anterior tibial glide persists on the tibia's medial condyle in part because the medial tibial articular surface is longer in the anterior-posterior dimension than the lateral tibial articular surface and in part due to the tension forces applied by the muscles and ligamentous stabilizers. This produces external tibial rotation, i.e., the "screw-home" mechanism.

In the final phase of extension, as the knee enters its final few habitual degrees of extension or hyperextension, the anterior cruciate ligament as well as both collateral ligaments are taut, and the knee is in its maximally stable position, with the leg able to support body weight despite the quad muscles being completely relaxed.

The full range of motion of a natural knee commonly is in the range of about 10°-15° of hyperextension up to about 140° to 155° of flexion and maximally up to about 165° in certain individuals. Most of the tibial rotation in lower flexion activities such as walking or stair climb occurs in the first 0-30° of flexion (70%). The knee has little rotational freedom in extension, thereby providing stability with low energy expenditure while standing. However, in natural deep flexion knee motion, there typically is an internal rotation of the tibia relative to the femur at angles of significant flexion of the knee joint, about 90° of flexion and greater. See Hollister, A. M., Jatana, S., Singh, A. K., Sullivan, W. W., and Lupichuk, A. G.: The Axes of Rotation of the Knee, Clin. Orthop. Relat. Res., 290, pp. 259-268; Roland M, Hull M L, Howell S M.: Virtual axis finder: a new method to determine the two kinematic axes of rotation for the tibio-femoral joint. J Biomech Eng. 2010 January; 132(1):011009; Hefzy M S, Kelly B P, Cooke T D, al-Baddah A M, Harrison L.: Knee kinematics in-vivo of kneeling in deep flexion examined by bi-planar radiographs. Biomed Sci. Instrum. 1997; 33:453-8; and Spanu C E, Hefzy M S.: Biomechanics of the knee joint in deep flexion: a prelude to a total knee replacement that allows for maximum flexion. Technol. Health Care. 2003; 11(3):161-81

By way of definition, internal rotation of the tibia refers to the tibia rotating about its longitudinal axis medially from an anterior perspective. For instance, looking down on one's own right tibia, in deeper flexion, the tibia rotates counter-clockwise relative to the femur as one flexes the knee in the direction of flexion. This internal rotation facilitates deep knee flexion by providing clearance for the soft tissue, e.g., ligaments, tendons, and muscles, surrounding the knee joint.

Additionally, the natural menisci of the knee are formed substantially of soft tissue such as cartilage and, therefore, are compressible, i.e., they can change shape. The menisci in a natural knee also move relative to the tibia during movement of the knee. However, current technology and materials for prosthetic knee articular components are not sufficiently advanced to provide shape change functionality. Rather, in prosthetic knees, the tibial articular surfaces (the replacement of the natural menisci) generally are made of a hard polymer such as polyethylene and are relatively stiff under physiologic loads. Also, most are fixedly attached to the tibia. The shape of the articulating surfaces, including the femoral condyles and the tibial plateau and the locations where the femur contacts the tibia versus the horns of the meniscii, have been nicely summarized by Freeman M A, Pinskerova V.: The movement of the normal tibio-femoral joint. J. Biomech. 2005 February; 38(2):197-208, pp 201-203.

Freeman et al also summarized the tibio-femoral rotational characteristics from full extension to deep flexion (pp 203-206).

Also, most TKR implants do not provide an extension-flexion range anywhere near the roughly 165° range of motion of a natural knee. Most TKR implants at this time provide a range of motion of about 10° of hyperextension to about 115° to 130° degrees of flexion, which is less than what is necessary or desirable for many common daily activities, such as kneeling, squatting, and certain sports activities.

SUMMARY OF THE INVENTION

In accordance with principles of the present invention, a total joint replacement prosthesis comprises at least two articular components, e.g., a femoral articular component and a tibial articular component in the case of a prosthetic knee, and includes features that help increase maximum flexion of the joint, facilitate longitudinal rotation of the bones relative to each other as well as more closely emulate the natural movement of the joint and provide other advantages. In accordance with one aspect of the invention, the medial and lateral femoral condylar articular surfaces have substantially uniform and equal radii from full extension (or hyperextension) up to about 90° of flexion. At 90° and greater flexion, the lateral condylar articular surface has a smaller radius than the medial condylar articular surface, but the surface of the medial condyle gradually becomes increasingly more proud than the surface of the lateral condyle to facilitate internal rotation of the tibia at deep flexion angles. In deepest flexion (145°-165°) the medial radius is smaller than the lateral, but the medial condylar surface remains more proud than the lateral condylar surface.

In accordance with another aspect of the invention, the tibial articular component includes medial and lateral compartments defining medial and lateral tibial articular surfaces, respectively, to accept the mating asymmetric femoral condyles. These tibial articular surfaces each have identical depths relative to the tibial resection, which facilitates soft tissue balancing particularly when the tibial bone is resected perpendicular to the mechanical axis of the limb.

In accordance with another aspect of the invention, the tibial articular component includes a post positioned intermediate the medial and lateral compartments that engages with a cam on the femoral articular component disposed between the medial and the lateral condylar articular surfaces. The cam and post are designed relative to each other to first become congruent with each other at flexion angles of approximately 60°-80° of flexion and to mate symmetrically during the first 20°-30° of congruency, and then mate asymmetrically at greater degrees of flexion, e.g., flexion angles greater than about 80° to 110° to force internal rotation of the tibia relative to the femur at the greater angles of flexion.

Instead of the post and cam configuration, the femoral articular component may include a ridge positioned intermediate the medial and lateral condyles and the tibial articular component may include a mating groove disposed between the medial and lateral tibial articular surfaces. The ridge and groove may be designed relative to each other to first become congruent with each other at flexion angles of approximately 60°-80° and to mate symmetrically. The ridge may be asymmetric in the coronal plane to force internal rotation of the tibia relative to the femur only at greater angles of flexion. The ridge-groove articulation also provides femoral roll-back and assists the medial tibio-femoral articulation in preventing posterior subluxation of the tibia relative to the femur in deeper flexion positions.

BRIEF DESCRIPTION OF THE DRAWINGS

FIG. 10A is a cross-sectional sagittal plane view of the femoral and tibial components of a prosthesis in accordance with the principles of the present invention taken through the approximate middle of the lateral condyle.

FIG. 10B is a cross-sectional sagittal plane view of the femoral and tibial components of a prosthesis in accordance with the principles of the present invention taken through the approximate middle of the medial condyle.

DETAILED DESCRIPTION OF THE INVENTION

Figure 1:
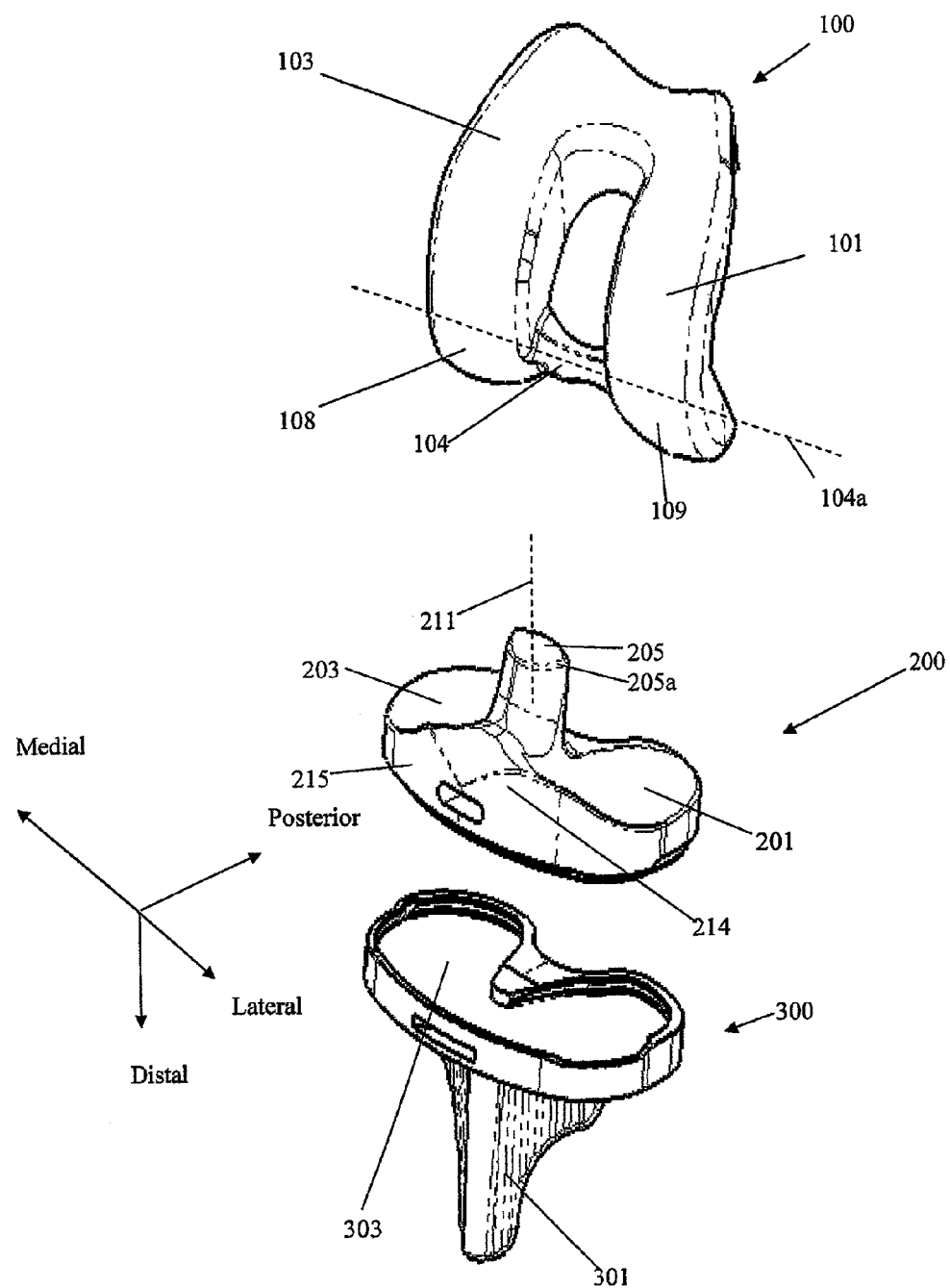
FIG. 1 is an exploded perspective view of the tibial and femoral articular components of a total knee replacement prosthesis for the right knee in accordance with the principles of the present invention.

FIG. 1 is an exploded view of several of the articular components of a TKR prosthetic implant in accordance with one embodiment of the invention. The implant comprises of a femoral articular component 100, a tibial articular component 200, and a tibial stem component 300. The femoral articular component 100 is placed on a patient's distal femur after appropriate resection of the femur. In some cases, to provide better support, the femoral articular component 100 may be mounted on a femoral stem (not shown) that is implanted into an intramedullary canal drilled into the distal femur. The femoral articular component 100 may be formed of any biocompatible material that is hard, durable, and has a relatively low coefficient of friction, such as polished cobalt chromium alloys, titanium alloys, or high molecular weight polyethylene. The femoral articular component 100 essentially replaces the condyles of the natural knee and therefore comprises two condylar articular surfaces, a medial articular surface 101 and a lateral articular surface 103. As best seen in the side view of FIG. 2, the femoral articular component 100 is substantially J-shaped.

The tibial articular component (sometimes called a "tray") 200 essentially replaces the natural menisci of the knee and usually is mounted on a stem structure 300, which includes a stem 301 and a plateau 303 for receiving the tibial articular component 200. The stem 301 extends into a surgically-formed hole in the intramedullary canal of the tibia. The tibial stem component 300 typically is formed of a biocompatible metal, such as titanium or cobalt chromium alloy, whereas the tibial articular component 200 or tray typically is formed of a low-friction polymeric material, such as high molecular weight polyethylene. The implants are further secured to the bone at the bone interface using either polymethylemethacrylate (PMMA) bone cement or a press-fit 3D porous structure, such as a commercially pure titanium plasma spray with or without a resorbable calcium phosphate coating (CaP), which facilitates bone on-growth/ingrowth. Since the femoral articular component 100 and the tibial articular component 200 essentially replace the articular femoral and tibial surfaces, respectfully, of the knee (i.e. the condyles of the femur and the menisci of the tibia, respectively), the medial and lateral condylar articular surfaces 101, 103 of the femoral articular component 100 sit in and rotate as well as translate within the medial and lateral compartments defining medial and lateral tibial articular surfaces 201, 203, respectively, of the tibial articular component 200.

As noted above, in the natural knee, the natural range of motion usually is from about +10° degrees of hyperextension to about 165° of flexion. Furthermore, at high degrees of flexion, e.g., greater than about 90° to 100° flexion, there is internal rotation of the tibia relative to the femur. However, most prosthetic knees provide a range of motion of only about +10° of hyperextension to about 90° to 130° of flexion. Furthermore, most current TKR prostheses do not well emulate natural internal rotation of the tibia relative to the femur. Many allow such rotation, but do not force it.

Figure 2:
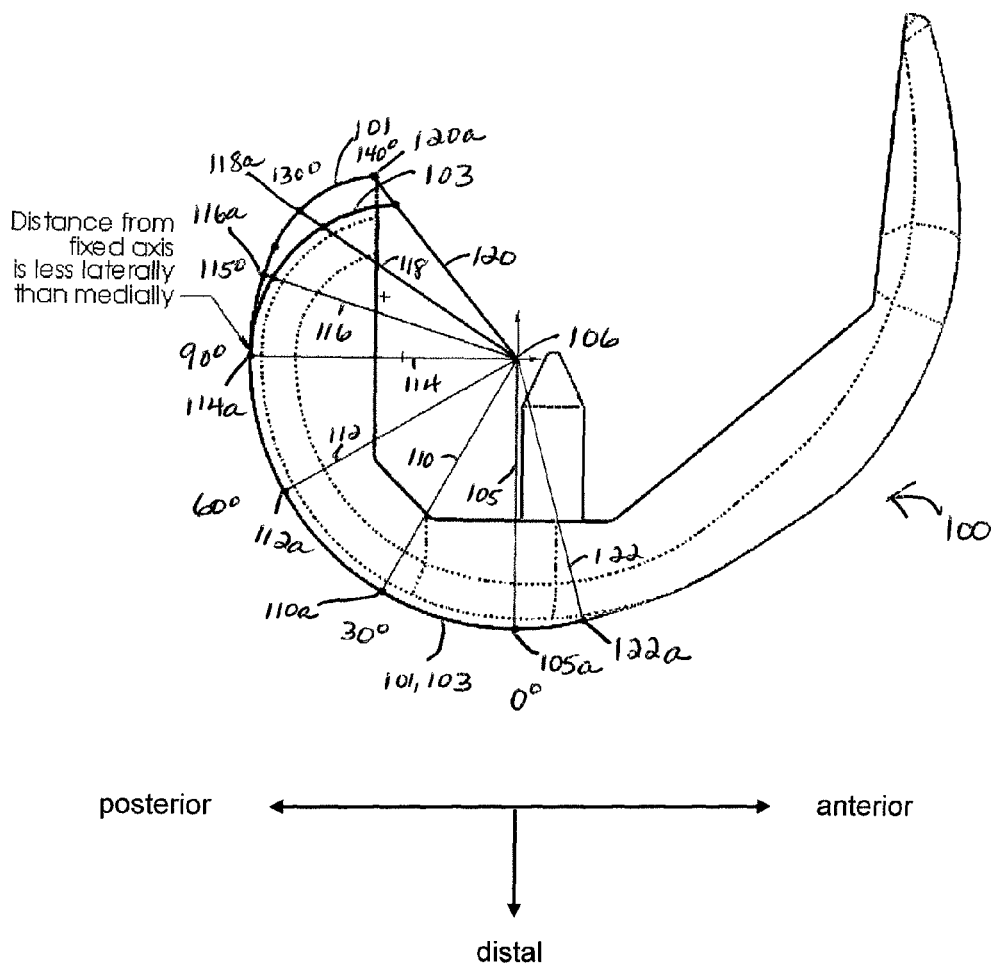
FIG. 2 is a lateral side view of the femoral articular component of the embodiment shown in FIG. 1.

Referring now to FIG. 2, which is a lateral side view (a sagittal plane view) of a right knee femoral articular component 100 illustrating a first aspect of the invention, the medial and lateral condylar articular surfaces 101, 103 are symmetric (equal) for most of their surfaces, but become asymmetric at their most posterior extend (corresponding to the deepest knee flexion). In FIG. 2, the femoral articular component 100 is shown in an orientation that would correspond to full extension of the knee (i.e., 0° flexion) if one were to assume that the tibial articular component 200 were positioned horizontally across the page just below the femoral articular component. Accordingly, in extension, the bulk of the load of the bearing of the femoral articular component 100 on the tibial articular component 200 would be along the vertical line 105 in the Figure. Point 106 at the top of line 105 corresponds to the center of the radius defining most of the radial surface of the condylar articular surfaces 101, 103 of femoral component 100 that may actually bear on the tibial articular surfaces 201, 203 of the tibial component 200 within about 100 to 130 degrees of motion provided by the prosthesis. Note that, although the center of curvature of the femoral implant changes beyond lines 114 and 116, respectively, the mating tibial articular surface shape curves superiorly in the posterior contact zones so that the relatively constant fixed axis of motion in the human femur is maintained by the articulating surfaces in conjunction with the muscles and ligamentous stabilizers.

The contact between the two articular surfaces of a joint is termed the congruency of the joint. The greater the contact area between the two articular surfaces, the higher the congruency. Accordingly, the concentration of the load on the femoral articular component bearing on the tibial component for a person standing with 0° knee flexion would be concentrated around the point 105a at the bottom of line 105, which corresponds roughly to the center of the congruency between the femoral articular component and the tibial articular component at 0° of flexion.

The other lines 110, 112, 114, 116, 118, and 120 radiating from point 106 correspond to other degrees of knee flexion as indicated in the drawing and the other end points 110a, 112a, 114a, 116a, 118a, and 120a roughly correspond to the centers of contact and congruency of the condylar articular surfaces 101, 103 with the tibial articular surfaces for those knee flexion angle ranges. (The locations depicted are approximate because the contact location varies with the tibial surface curvature and the degree of lateral rotation.)

In accordance with one embodiment of the invention, the saggittal radii of both the medial and lateral condylar articular surfaces 101, 103 of femoral articular component 100 are equal to each other and uniform (i.e., have a constant radius) from at least 10° of hyperextension to 90° of flexion. Thus, assuming that the lateral and medial compartments 201, 203 of the tibial articular component also are symmetric with each other and are relatively flat, nonarcuate and minimally constrainingthen articulation of the femoral articular component 100 on the tibial articular component 200 will induce no rotation of the tibia relative to the femur about the longitudinal axis of the tibia. (Note that, in certain instances, tibio femoral articulation can be designed to force rotation using symmetric, highly congruent (i.e., more constraining) contact geometries formed into an arcuate path similar in shape to a kidney bean. The implant geometries and the motion generated can accurately replicate the human knee.) However, for relative orientations of the femoral articular component 100 and the tibial articular component 200 corresponding to angles of knee flexion of 90° and greater, the medial and lateral condylar articular surfaces 101 and 103 are asymmetric. Particularly, for knee flexion angles of 90° and greater, the lateral condylar articular surface of the femur 103 has a smaller radius of curvature than the medial condylar articular surface 101. This asymmetry causes the medial condylar articular surface 101 to become increasingly more proud relative to the lateral condylar articular surface 103 as the angle of flexion increases above 90°. In turn, during rolling motions (as opposed to gliding/sliding motions), this will cause the tibial articular component 200 to rotate about a longitudinal axis of the tibia internally relative to the femoral articular component 100 against which it is articular. Because the mating tibial surface is curved upwards (superiorly) on the posterior lateral side to increase the sagittal plane congruency, (which is unlike the normal anatomy, which is curved downward (distally) on the posterior lateral surface and has conformable meniscal shapes), the reduced profile of the lateral condyle prevents over stuffing of the joint posteriorly in flexion. That, in turn, facilitates normal rollback motion, with or without obligatory tibial internal rotation. In effect, this means that beyond 90° flexion, the tibia is allowed to rotate internally relative to the femur during sliding motions and will rotate internally during rolling motions without being blocked due to excessive ligament tension. At knee flexion angles of less than 90°, there will be minimal surface-geometry-enforced internal rotation of the tibia relative to the femur. However, varying degrees of both internal and external rotation about the mechanical lateral rotation axis, which is not coincident with the tibial anatomic axis, is either constrained or allowed by the specific geometries of the medial and lateral compartments.

In one embodiment, the medial condylar articular surface 101 has a constant radius over substantially its entire surface, whereas, the lateral condylar articular surface 103 has the same, constant radius as the medial condylar articular surface at surface points corresponding to the center of congruency of the medial condylar articular surface 103 with the medial tibial articular surface 203 corresponding to knee flexion angles up to 90° of knee flexion and then a decreased radius corresponding to knee flexion greater than 90°. Thus, the lateral and medial condylar articular surfaces 101, 103 are equal and of constant radius between points 105a and 114a. In fact, preferably, the equal and constant radii conditions hold true to the full extent of knee extension permitted by the prosthesis, e.g., approximately 10° to 15° of hyperextension (as illustrated by line 122 and point 122a).

In a practical embodiment, the very end of the medial condyle 101 (corresponding to the deepest knee flexion) actually will have a decreased radius relative to the remainder of the medial condylar articular surface so as to avoid extremely high stress line congruency between the femoral articular component and the tibial articular component at the end of the range of motion in flexion. This is illustrated in FIG. 2, where it can be seen that the radius of the medial condylar surface is decreased starting above line 116a (corresponding to about 110° to 130° of knee flexion) up to the end of flexion at line 120, which, at the tip, corresponds to about 163° to 167° of knee flexion.

The internal rotation of the tibia at deep angles of flexion (e.g. 90° to 155° flexion) facilitates soft tissue balancing and congruency of the femoral articulating surfaces with the tibial articular surfaces and provides a much more natural feeling motion in the prosthetic knee.

In at least one preferred embodiment, the medial and lateral condylar articular surfaces 101, 103 have identical medial-lateral and sagittal radii over the typical range of motion, e.g., plus 10° of hyperextension to full flexion (about 155°).

In the natural anatomy of the knee, the tibio-femoral axis of rotation has been shown to be relatively fixed in the femur and offset and the anatomic medial and lateral condyles have constant, but different, sagittal radii from about +15° of hyperextension to about 130 to 140 degrees of flexion as described by Freeman M A, Pinskerova V., The movement of the normal tibio-femoral joint, J. Biomech. 2005 February; 38(2):197-208. The natural tibial articular surface also has a varus slope. Further, the proximal end of the natural tibia, upon which the lateral and medial menisci are disposed, is sagittally concave. To facilitate flexion and extension soft tissue tension (gap), balance, and restoration of the mechanical axis of the leg, most surgeons remove the varus slope at the proximal end of the tibia when cutting the tibia for TKR, i.e., they cut the proximal end of the tibia orthogonally to the mechanical axis of the extended leg, rather than with the slight varus slope at the proximal end of the natural tibia.

Like most implants, the implant of the present invention preferably has equal medial and lateral tibial articular minimum surface thicknesses relative to this tibial cut. Accordingly, the tibial varus angulation of the natural knee is removed in the TKR prosthetic knee. With this anatomic tibia varus angulation removed, the femoral implant condylar articular surfaces in the inventive prosthesis have equal or approximately equal medial and lateral sagittal radii between about +10° of hypertension to about 90° of flexion to restore normal, balanced, equalized flexion and extension gaps in the knee.

In the natural knee, beyond about 90° of flexion, the lateral tibial articular surface (comprised of the lateral meniscus which is more translatable relative to the tibia than the medial meniscus, and the sagittally convex curvature of the lateral tibial articular facet) is lower than the medial articular surface. Thus, when the tibial articular surface of an implant maintains a relatively equal medial and lateral thickness and a slight concave surface on both the medial and lateral sides, which is done to improve deep flexion articular surface congruency, and to minimize stress on the implant and deep flexion positions, the posterior lateral surface location relative to the femoral bone axis of rotation must be reduced in size relative to the medial femoral condylar articular surface to facilitate sufficient clearance. The reduction of the radius of the medial condylar articular surface 101 relative to the lateral condylar articular surface 103 in the present invention compensates for all of (1) the inability of the tibial articular surface to change shape like the normal lateral meniscus (particularly, the posterior horn), (2) the clearance lost due to the absence of a greater lateral articular surface slope compared to the medial side and the absence of a convex sagittal shape of the underlying lateral tibial bone, and (3) the inability of the tibial articular surface to move in three dimensional space, like the natural lateral meniscus, which articulates in the posterior horn in deep flexion.

The above-described design of the medial and lateral condylar articular surfaces 101, 103 of the femoral articular component 100 causes the lateral articular surface to be closer to the femur's tibio-femoral axis of rotation than the medial condylar articular surface.

Figure 3A:
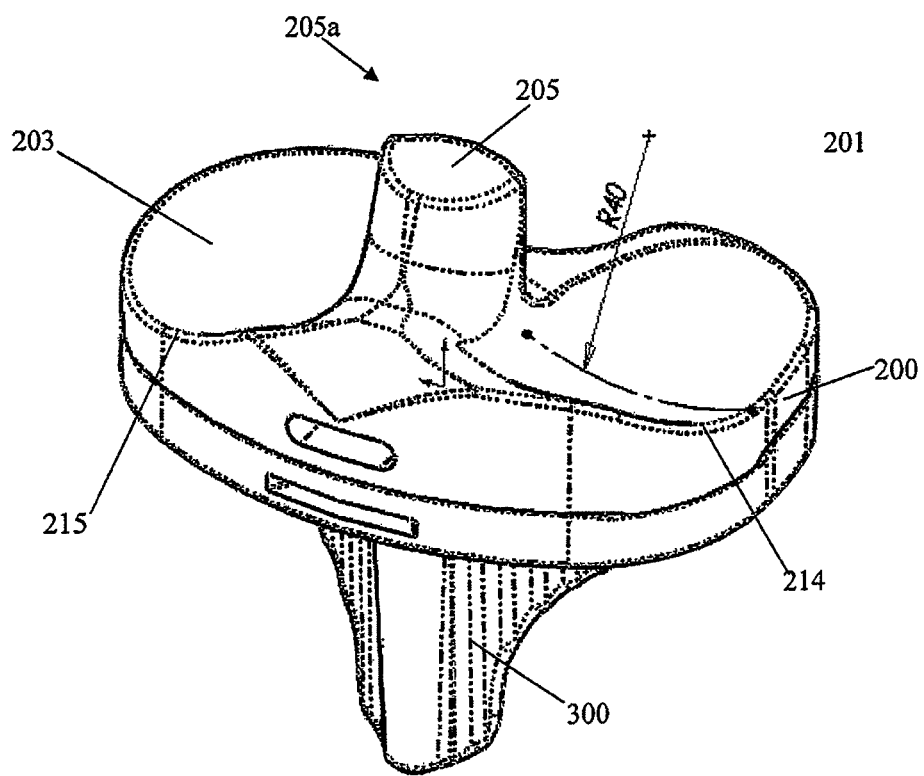
FIG. 3A is a perspective view of the tibial articular component of the embodiment shown in FIG. 1.
Figure 3B:
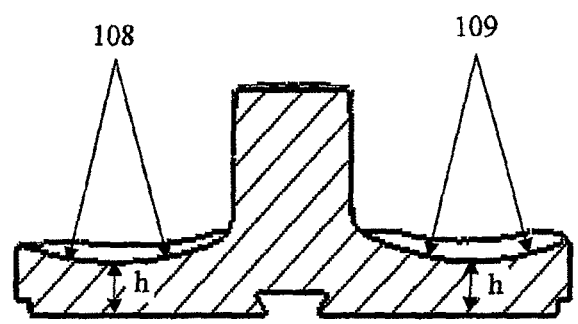
FIG. 3B is a cross-sectional anterior view of the tibial articular components of the embodiment shown in FIG. 1 demonstrating the minimum thicknesses of the lateral and medial tibial articular compartments.

With reference to FIGS. 3A and 3B, in one embodiment, the lateral and medial articular compartments 201 and 203 of the tibial articular component 200 have equal minimum thickness, t, and symmetric curvatures in both the sagittal direction and the coronal (i.e., medial-lateral) direction. In one embodiment, the articular surfaces of both the medial and lateral compartments 201, 203 are substantially concave torroidal surface segments (i.e., the interior surface of a hollow torroid). That is, the radius of the surface in the sagittal plane differs from the radius of the surface in the coronal plane. For clarity, note that, if the radius in the coronal plane and radius in the sagittal plane were equal, it would be an interior/concave spherical surface, rather than an interior/concave torroidal surface).

In one embodiment, the lateral and medial condylar articular surfaces 101, 103 have constant and equal coronal radii 108 and 109.

Figure 4A:
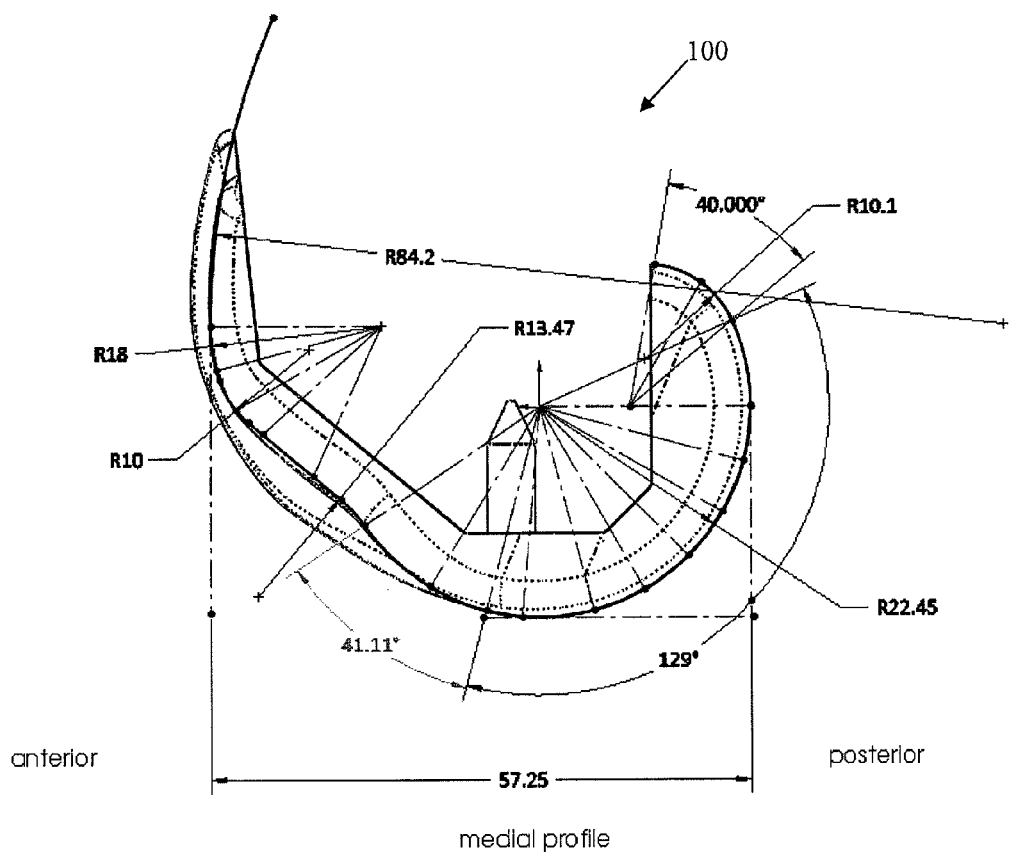
FIG. 4A is a medial side view of the femoral articular component of the embodiment shown in FIG. 1 with exemplary dimensions shown.
Figure 4B:
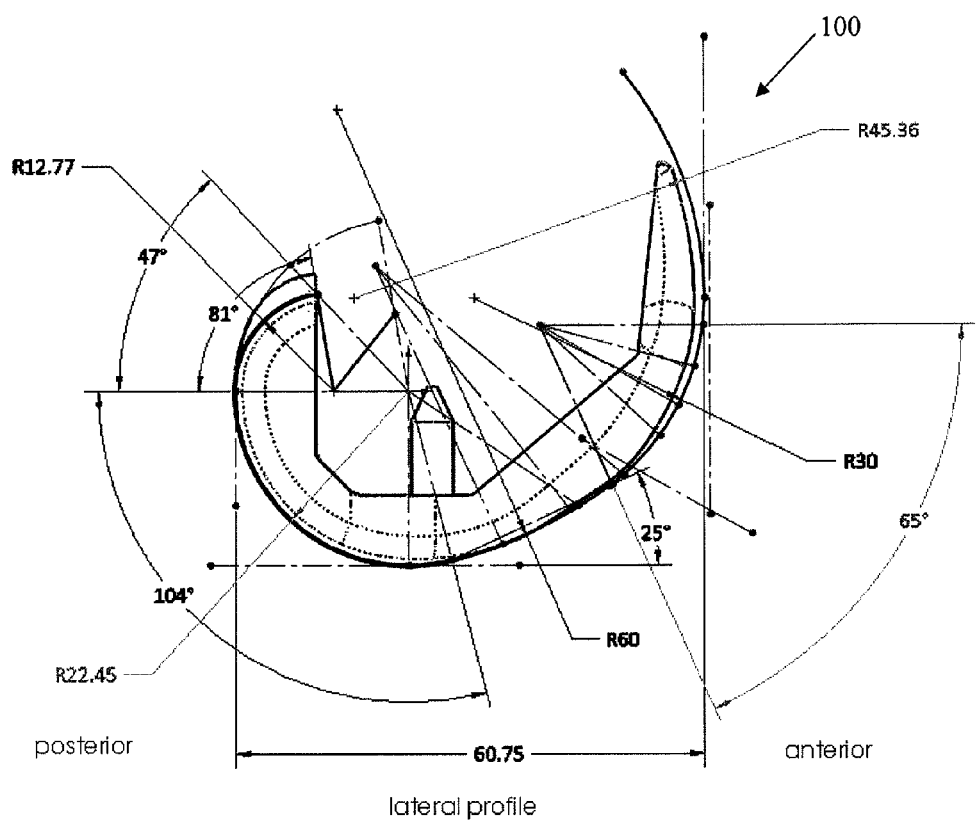
FIG. 4B is a lateral side view of the femoral articular component of the embodiment shown in FIG. 1 with exemplary dimensions shown.

FIGS. 4A and 4B show a medial profile and a lateral profile, respectively, of one particular femoral articular component 100 in accordance with a particular embodiment of the invention with the sagittal radii of the various segments of the medial and lateral condylar articular surfaces, respectively, defined. It should be understood that the absolute values of the various radii in FIGS. 4A and 4B would be dependent on the size of the implant (which, of course, depends on the size of the patient). However, the ratios of the various radii to each other are instructional. Nevertheless, the values shown in FIGS. 4A and 4B still are exemplary and not limiting.

Referring again to FIG. 1, in accordance with another aspect of the invention, a post 205 is provided on the tibial articular components 200 that mates with a cam 104 on the femoral articular component 100. The post 205 extends cranially (i.e., upwardly) from the tibial articular component 200 and is located between the medial and lateral articular surfaces 201 and 203. The cam 104 on the femoral articular component 100 runs laterally in the coronal direction between the lateral and medial condylar articular surfaces 101 and 103. The incorporation of a posts and cams in TKR prostheses is known. See, for instance, U.S. Pat. No. 7,326,252, which is incorporated herein fully by reference. However, in accordance with this aspect of the inventive prosthesis, the post and cam are adapted to provide symmetry for lower angles of flexion and asymmetry for higher angles of flexion to further facilitate the inward rotation of the tibia relative to the femur only at deeper angles of flexion.

Figure 5A:
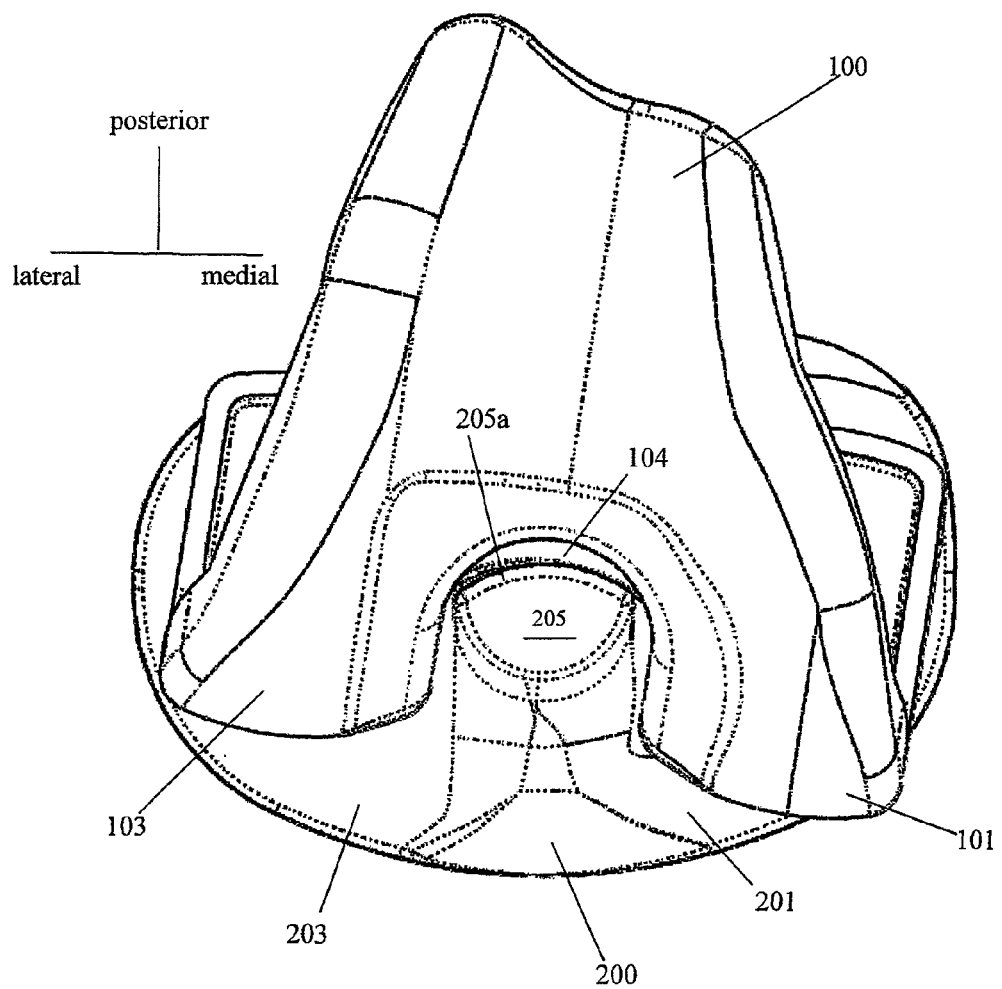
FIG. 5A is a top view of sub-embodiment of the femoral and tibial articular components of the embodiment shown in FIG. 1 in the relative positions for a knee at an angle of flexion of about 90°.
Figure 5B:
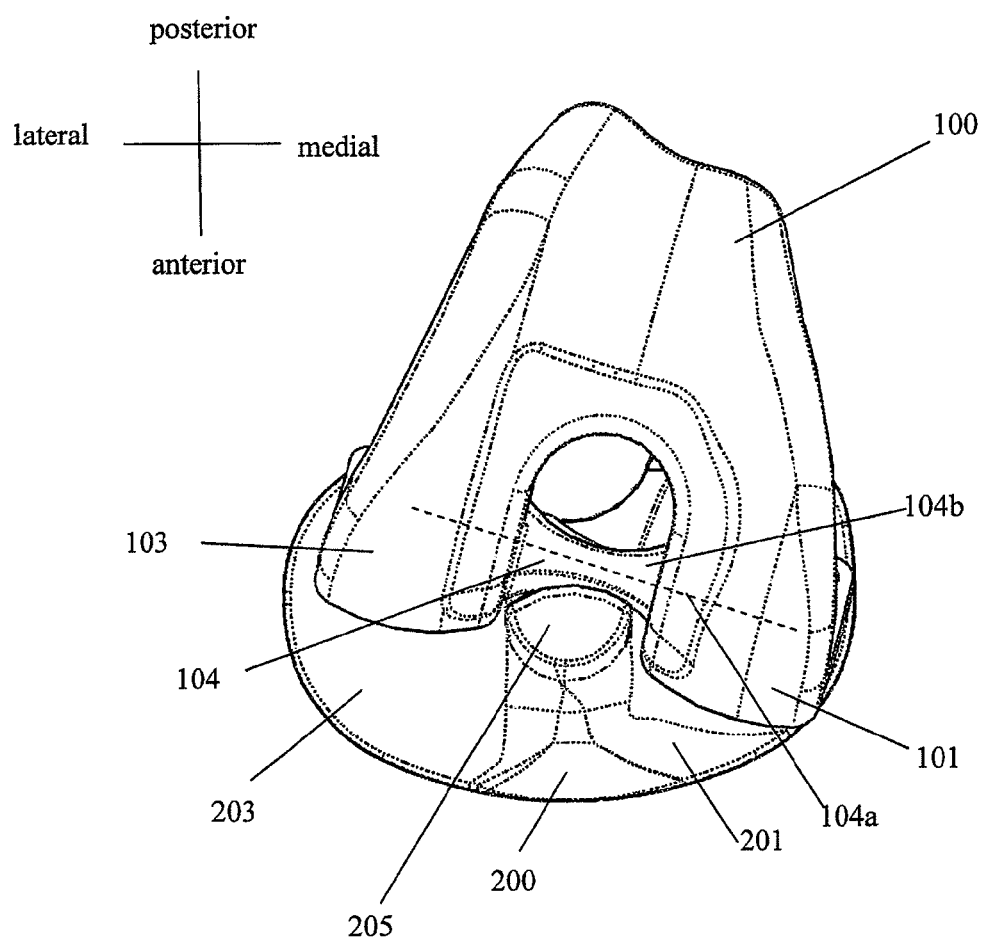
FIG. 5B is a top view of the sub-embodiment of the femoral and tibial articular components of the embodiment shown in FIG. 1 in the relative positions for a knee at an angle of flexion of about 150°.

FIGS. 5A and 5B are overhead plan views of the femoral articular component 100 and the tibial articular component 200 illustrating the interaction of the post 205 and cam 104 in accordance with one embodiment of the invention at two different angles of knee flexion. In one embodiment, the post 205 and cam 104 are positioned relative to each other (and the other anatomy of the knee, including the ligaments, muscles, and tendons) so that the cam is posterior of the post and they do not contact each other at knee flexion/extension angles less than about 60°-80°, and, preferably, about 70° flexion and become congruent (i.e., contact each other) only at knee flexion angles of approximately 70° and greater. Additionally, for the first 20° to 30° of deeper flexion after initial contact, the congruent surfaces of both the cam and the post are symmetric so as not to apply any rotational force of the tibia about its longitudinal axis relative to the femur. However, after the first 20° to 30° of deeper flexion after initial contact, an asymmetry in the cam does become congruent with the post so as to cause internal rotation of the tibia relative to the femur.

FIG. 5A shows the relative position of the femoral articular component 100 and the tibial articular component 200 at approximately 70° of flexion, i.e., when they make initial contact. FIG. 5B shows the relative position of the femoral articular component 100 and the tibial articular component 200 at approximately 130° of knee flexion. In this embodiment, the articular surface 205a of the post is symmetric and is essentially a portion of a cylindrical surface. The surface of the cam 104 is substantially catenoid in shape in order to provide maximal congruency with the cylindrical surface 205a of post 205 as the cam revolves around its longitudinal axis 104b relative to the tibial component 200.

However, the cam 104 is longitudinally asymmetric (i.e., in the medial-lateral (or cranial) direction) over only a radial portion of its surface so as to cause internal rotation of the tibia relative to the femur over the corresponding portion of the angular range of motion of the knee joint. More particularly, in one embodiment, the surface of the cam 104 is longitudinally symmetric for the radial segment of the surface that corresponds to knee flexion-extension angles less that approximately 70° of flexion (e.g., for +10° of hyperextension to 90° of flexion). Thus, within that range of motion, the interaction of the post 205 and cam 104 is neutral in that it does not apply any force between the two tending to force the tibial articular component 200 to rotate to any particular angular orientation around the tibia's longitudinal axis relative to the femoral articular component 100. Of course, other forces, such as the ligaments and tendons as well as the forces between the condylar articular surfaces 101, 103 and the tibial articular surfaces 201, 203 may apply forces between the femoral and the tibial articular components tending to orient them in certain angular orientations about the lateral rotation axis of the knee, which is similar to, but not coincident with, the longitudinal axis of the tibia which, in turn, roughly corresponds to the mechanical axis of the leg.

However, as can probably best be seen in FIG. 5B, the surface of the cam 104 is longitudinally and radially asymmetric. Specifically, it is enlarged at portion 104a. Specifically, the cam surface is radially expanded toward the lateral longitudinal end of the cam relative to the medial longitudinal end of the cam over a radial portion of the cam surface corresponding to knee flexion angles of approximately 90° flexion to approximately 155° flexion. Accordingly, at angles of knee flexion of approximately 90° and greater, the surface contact between the cam 104 and the post 205 does apply a force causing the tibial articular component 200 to roll internally relative to the femoral articular component 100. This helps the tibia rotate internally about its longitudinal axis relative to the femur at deeper angles of flexion.

At approximately 130° of flexion as shown in FIG. 5B, the asymmetric portion 104a of the cam 104 has now come into contact with the articular surface 205a of the post 205, causing the tibial articular component 200 to rotate internally relative to the femoral articular component 100 (i.e., the tibial articular component has rotated counter-clockwise relative to the femoral articular component in the view of FIG. 5B).

In accordance with this aspect of the invention, the cam and the post interaction allows internal rotation of the tibia relative to the femur at the lower angles of flexion, but does not force it. However, at the higher angles of flexion, it helps force the internal rotation of the tibia relative to the femur.

The post 205 and cam 104 are positioned on the tibial and femoral articular components, respectively, so that they do not contact each other until the knee has reached about 60° to 80° of flexion. Thus, in use, the femoral articular surfaces 101, 103 can substantially slide (or shear) on the tibial articular surfaces 201, 203 at lower angles of flexion (including hyperextension) before the cam 104 engages the post 205. After the cam 104 contacts the post 205, that engagement will assist in causing more of a rolling articulation of the femoral articular surfaces 101, 103 on the tibial articular surfaces 201, 203 at higher degrees of flexion.

Further, the TKR implant of the present invention may be medially stabilized. Specifically, while the medial tibial articular surface 201 may have the same general stabilized shape, but it may have a different size. The medial tibial articular surface 201 may be smaller (e.g., comprise a segment of a smaller torroidal surface shape) than the lateral tibial articular surface 203 so that the medial tibial articular surface and medial condyle are more congruent with each other than the lateral tibial articular surface and lateral condyle are with each other. This is best seen in FIGS. 10A and 10B. FIG. 10A is a cross-sectional sagittal plane view of the femoral and tibial components 100, 200 of the prosthesis taken through the approximate middle of the lateral condyle 103 (akin to section A-A in FIG. 7A). FIG. 10B is a cross-sectional sagittal plane view of the prosthesis taken through the approximate middle of the medial condyle 101 (akin to section B-B in FIG. 7A). As can be seen, the medial mating tibial and femoral articular surfaces 101, 201 are more congruent than the lateral mating tibial and femoral articular surfaces 103, 203. Such a design causes the medial and lateral tibial articular surfaces 200 to have a relatively higher wall (or lip) 214 is more substantial and steeper at its anterior end than the lateral tibial articular surface 203. It is desirable for the wall 215 at the anterior end of the medial tibular articular surface to be at least about 8 mm higher than the wall 215 at the anterior end of the lateral tibular articular surface.

Such a design helps prevent the medial condylar articular surface 103 of the femoral articular component 100 from sliding anteriorly off of the medial articular surface 201 of the tibial articular component 200 (i.e., the high medial lip prevents posterior subluxation of the tibia relative to the femur). Specifically, due to the larger radius of the posterior medial condylar articular surface 101 relative to the posterior lateral condylar articular surface, the medial condylar articular surface 101 will roll farther on the medial tibial articular surface 201 than the lateral condylar articular surface 103 will roll in the lateral tibial articular surface 203 (if it purely rolls with no sliding/shearing). However, the steeper surface at the anterior end of the medial articular surface 201 will tend to cause greater sliding/shearing (as opposed to rolling) on the medial side than on the lateral side. The combined interaction of greater medial congruency (stability) and the central articulating post allows for soft transition from a substantially sliding motion to a substantially rolling motion (femoral roll back). In use, the medial condylar articular surface 101 does not slide anteriorly or posteriorly more than about 3-6 millimeters on the medial tibial articular surface 201. At lower flexion angles, up to about 60° to 70°, the anterior lip 214 prevents anterior translation as the cam 104 is rolled onto the post 205. This is consistent with the reduced translation of the medial tibial articular bone compartment relative to the kinematic flexion-extension axis of the human distal femur of less than about 12 mm on the medial side compared to about 20 mm of relative motion on the lateral side from full extension to 120 degrees of flexion as documented in cadaveric studies by Walker et al. (Walker P S, Heller Y, Yildirim G, Immerman I.: *Reference axes for comparing the motion of knee replacements with the anatomic knee. Knee.* 2011 October; 18(5): 312-6. Epub 2010 Aug. 17.)

Greater congruency on the medial side than on the lateral side has several other benefits. For instance, lower sagittal congruency posteriorly on the lateral side combined with reduced surface location on the posterior lateral femoral implant surface (r2) as compared to the posterior medial articular surface allows for greater laxity in lateral tibio-femoral articulation in deep flexion, thereby facilitating greater lateral side roll back coupled with internal rotation of the tibia relative the femur in these deeper flexion positions.

Furthermore, greater medial sagittal congruency both anteriorly and posteriorly in extension provides stability to the knee. This stability is critical to help prevent tibio-femoral dislocation in the face of marked ligament laxity, imperfect ligament balance (such as flexion-extension gap mismatch), loss of ligament integrity/tension (which may be caused by excessive release of the posterior-lateral structures, excessive lateral release with damage to the popliteus tendon and lateral collateral ligaments), extensor mechanism incompetence, or a strong contraction of the hamstring when the knee is in flexion causing a jump of the femoral component over the tibial polyethylene articular component 200. In deeper flexion, this congruency reduces the translation of the contact location medially, mimicking the normal knee, where lateral translation of the contact point is greater. This conformance also facilitates normal rotation about the natural lateral rotation axis of the knee (as described in the Hollister, A. M., Jatana, S., Singh, A. K., Sullivan, W. W., and Lupichuk, A. G., The Axes of Rotation of the Knee, *Clin. Orthop. Relat. Res.*, 290, pp. 259-268 and Roland M, Hull ML, Howell S M, Virtual axis finder: a new method to determine the two kinematic axes of rotation for the tibio-femoral joint. J Biomech Eng. 2010 January; 132(1):011009.

Additionally, the laxity on the lateral side allows for more relative translation of the contact point between the femur and the tibia as found in the normal knee. See Hefzy M S, Kelly B P, Cooke T D, al-Baddah A M, Harrison L., Knee kinematics in-vivo of kneeling in deep flexion examined by bi-planar radiographs, *Biomed Sci Instrum.* 1997; 33:453-8; Spanu C E, Hefzy M S., Biomechanics of the knee joint in deep flexion: a prelude to a total knee replacement that allows for maximum flexion, *Technol Health Care.* 2003; 11(3):161-81; Hefzy M S, Aeschliman, K L, Dennis, M J., Contact locations of the knee joint in deep flexion, *Journal of Biomechanics,* 2006, Vol 39(Suppl 1), ORS Oral Presentation #7048; Fukagawa S, Matsuda S, Tashiro Y, Hashizume M, Iwamoto Y., Posterior displacement of the tibia increases in deep flexion of the knee, *Clin Orthop Relat Res.* 2010 April; 468(4):1107-14. Epub 2009 Oct. 22; and Freeman M A, Pinskerova V., The movement of the normal tibio-femoral joint, *J Biomech,* 2005 February; 38(2):197-208.

The lateral tibial articular surface coronal congruency is slightly lower than the medial coronal congruency to facilitate greater rotation and translation on the lateral side of the tibio-femoral articulation. The greater congruency and higher lip of the medial articulation provides anterior-posterior stability and facilitates (allows) rotation of the tibio-femoral articulation about the anatomic lateral rotation axis, which is offset somewhat medially and anteriorly relative to the central tibial spine in the normal knee 1 Hefzy M S, Kelly B P, Cooke T D, al-Baddah A M, Harrison L., Knee kinematics in-vivo of kneeling in deep flexion examined by bi-planar radiographs, Biomed Sci Instrum. 1997; 33:453-8. Spanu C E, Hefzy M S., Biomechanics of the knee joint in deep flexion: a prelude to a total knee replacement that allows for maximum flexion, Technol Health Care. 2003; 11(3):161-81. The asymmetric tibial articular surfaces combined with equal medial and lateral distal thicknesses, different levels of sagittal plane congruency, and different, but similar, coronal plane conformity allows more normal tibio-femoral motion and stability.

In preferred embodiments, the cam and the post are designed so that they first make contact at 60° to 80° of flexion, and preferably about 70°. Furthermore, the asymmetry of the cam is designed so that the asymmetric portion of the cam does not become congruent with the articular surface 205a of the post 205 until approximately 20°-30° flexion beyond initial contact, e.g., 20° to 30° beyond 60° to 80° flexion (or 80° to 110° of flexion).

Figure 6A:
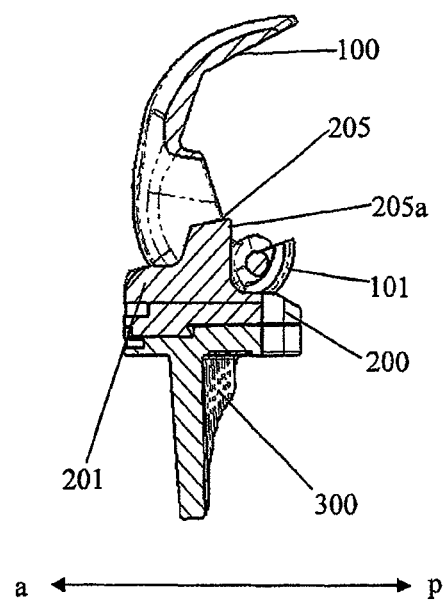
FIG. 6A is a cross-sectional lateral side view of the embodiment of FIG. 1, showing the femoral and tibial articular components in the relative positions for a knee at an angle of flexion of about 70° flexion.
Figure 6B:
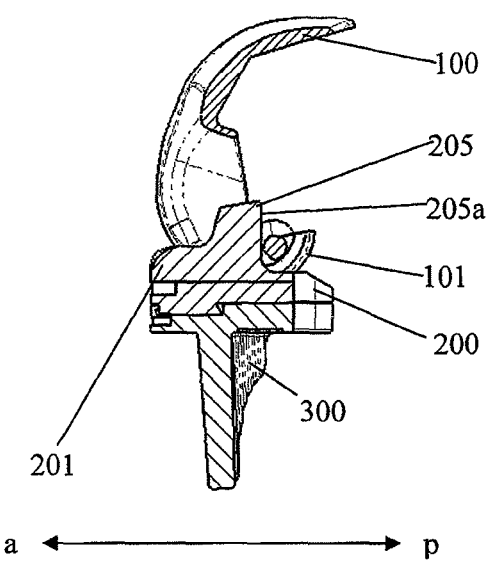
FIG. 6B is a lateral side view of the embodiment of FIG. 1, showing the femoral and tibial articular components in the relative positions for a knee at an angle of flexion of about 80° flexion.
Figure 6C:
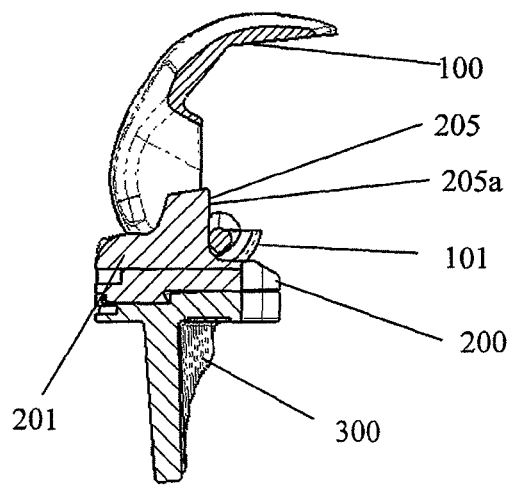
FIG. 6C is a lateral side view of the embodiment of FIG. 1, showing the femoral and tibial articular components in the relative positions for a knee at an angle of flexion of about 90° flexion.

FIGS. 6A, 6B, and 6C are medial side (i.e., sagittal plane) views of the prostheses of the present invention shown at flexion angles of 70°, 80° and 90°, respectively. In the particular embodiment illustrated in FIGS. 6A-6C, the post 205 and cam 104 are designed to engage each other at 80° of flexion. Thus, in FIG. 6A, the cam 104 has not yet contacted the post 205. Note that the medial condylar articular surface 101 is substantially congruent with the anterior portion of the medial articular surface 201 of the tibial articular component 200. Thus, the fact that the medial articular surface 101 has a steep surface at its anterior extent is helping prevent the medial condylar articular surface 101 from rolling further anteriorly. Specifically, it tends to cause greater sliding/shearing between the two mating articular surfaces 101, 201 (as opposed to rolling) than might occur with a less steep surface.

At 80° of flexion as shown in FIG. 6B, the cam 104 has just made contact with the post 205. In this position, the medial condylar articular 101 surface is still substantially congruent with the anterior portion of the medial tibial articular surface 201 of the tibial articular component 200.

Next, in FIG. 6C, at 90° of flexion, the cam 104 and post 205 have begun interacting with each other, but only in the symmetric zone so that no internal rotation of the tibia has yet been forced. Note that the congruency between the medial condylar articular surface 101 and the medial articular surface 201 of the tibial articular component 200 has now moved posteriorly, signifying that the medial condylar articular surface 101 has begun to roll back posteriorly on the medial tibial articular surface 201.

In other embodiments, the articular surface of the post may be made asymmetric, while the cam remains fully symmetric. In yet other embodiments, a combination of asymmetries on a cam and post maybe implemented.

Figures 7A, 7B, 7C:
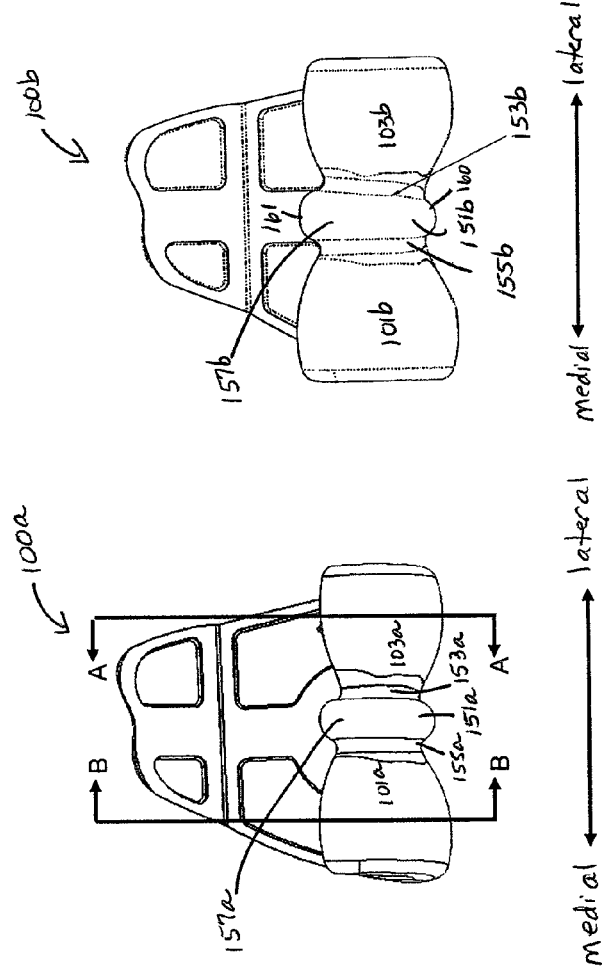
FIG. 7A is a distal end view of an alternative embodiment of a femoral articular component in accordance with the invention.
FIG. 7B is a distal end view of another alternative embodiment of a femoral articular component in accordance with the invention.
FIG. 7C is a proximal end view of a tibial articular component in accordance with an alternate embodiment of the invention.

FIGS. 7A, 7B, 7C, 8A, 8B, 9A, 9B, 9C, and 9D illustrate yet another embodiment having substantially the same effect as the post/cam feature discussed hereinabove in connection with FIGS. 5A, 5B, 6A, 6B, and 6C. In this embodiment, an alternative femoral articular component 101a shown in one configuration in FIG. 7A has a ridge 151a (instead of a cam), and an alternative tibial articular component 200a shown in FIG. 7C has a groove 251a longitudinally oriented in the sagittal direction (instead of a post) for receiving the ridge 151a. More particularly, FIG. 7A illustrates the femoral articular component 100a in accordance with this type of embodiment having a laterally-medially symmetric ridge 151a such that internal rotation of the tibia relative to the femur is allowed, but not forced.

FIG. 7B shows a similar alternate embodiment of a femoral articular component 100b having a slightly different ridge 151b that is medially-laterally asymmetric so as to actually force internal rotation of the tibia. Specifically, in the embodiment of FIG. 7A the lateral and medial side edges 153a and 153a, respectively, of the ridge are symmetric to each other and substantially parallel to the sagittal plane (in and out of the page in FIGS. 7A and 7B). However, in the embodiment of FIG. 7B, the lateral and medial side edges 153b and 153b, respectively, of the ridge are asymmetric in that the medial edge 155b is still substantially parallel to the sagittal plane, but the lateral side edge 153b slopes laterally outwardly in the upward direction in the view of FIG. 7B. This corresponds to the portion of the ridge 151b that will be within the groove 251a becoming wider (with the increased width effectively appearing on the lateral side) for increasing knee flexion. In the view of FIG. 7B, only the portion of the ridge 151b that corresponds to about 80° flexion to full flexion (about 155° is seen). Specifically, reference numeral 160 refers to the portion of the ridge 151b that will be the center of congruency with the groove 251a at 80° of flexion and reference numeral 161 refers to the portion of the ridge 151b that will be the center of congruency with the groove 251a at 155° of flexion.

The remainder of the ridge that is not seen in FIG. 7B may be laterally-medially symmetric (as in the embodiment of FIG. 7A) so that the forcing of internal rotation of the tibia relative to the femur only occurs at knee flexion angles of 80° and greater. The 80° flexion angle for commencing internal rotation in this embodiment is merely exemplary. As discussed above in connection with the post and cam embodiment of FIGS. 5A, 5B, 6A, 6B, and 6C, preferably, the forcing of internal rotation of the tibia relative to the femur begins somewhere between 80° and 110°.

Referring to FIG. 7C, which shows the alternative tibial articular component 200a that may be used with either of the two alternative femoral articular components 100a and 100b of FIGS. 7A and 7B, it comprising a groove 251a between the medial and lateral articular surfaces 201a and 203a in which the ridge 151a or 151b of the femoral articular component 200a or 200b will travel. The lateral and medial side walls 253a, 255a, respectively, of the groove 251a may be straight and substantially parallel to the sagittal plane. Alternately (and as shown in FIG. 7C), the medial side wall 255a may be substantially straight and parallel to the sagittal plane, but the lateral side wall 253a may curve inwardly in the anterior to posterior direction. Such a curve will help force the internal rotation of the tibia relative to the femur for either femoral articular component 100a or 100b. Specifically, an inwardly curved lateral wall 253a will tend to better force the tibial articular component 200a to rotate relative to the femoral articular component 100a or 100b, rather than slide/shear laterally relative to the femoral articular component, in response the engagement of side edge 153a or 1553b with side wall 253a.

In both embodiments, the groove 251a is wider than the ridge 151a, 151b. thus, in the symmetric embodiment represented by the combination of the femoral articular component 100a of FIG. 7A and the tibial articular component 200a of FIG. 7C, the combination prevents tibial external rotation relative to the femur in deeper flexion angles, e.g., 120° of flexion and greater, and allows (but does not force) tibial internal rotation relative to the femur.

In the alternate embodiment represented by the combination of the femoral articular component 100b of FIG. 7B and the tibial articular component 200a of FIG. 7C, internal rotation of the tibia is actually guided or forced by the interaction of the ridge 151b with the groove 251a.

Figure 8A:
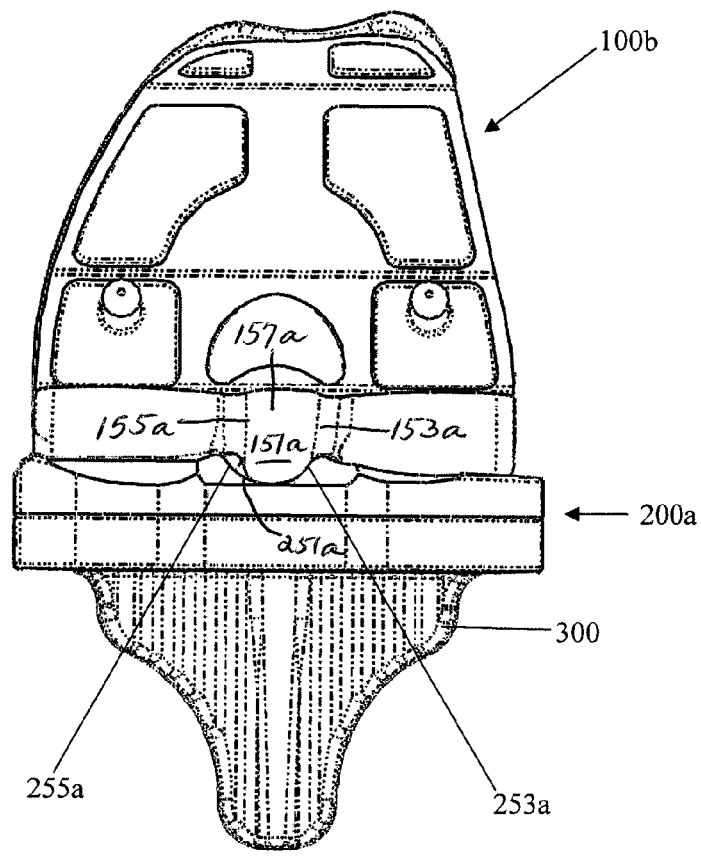
FIG. 8A is an assembled anterior-posterior view from the posterior of the femoral and tibial articular components of FIGS. 7B and 7C at approximately 90° of flexion.
Figure 8B:
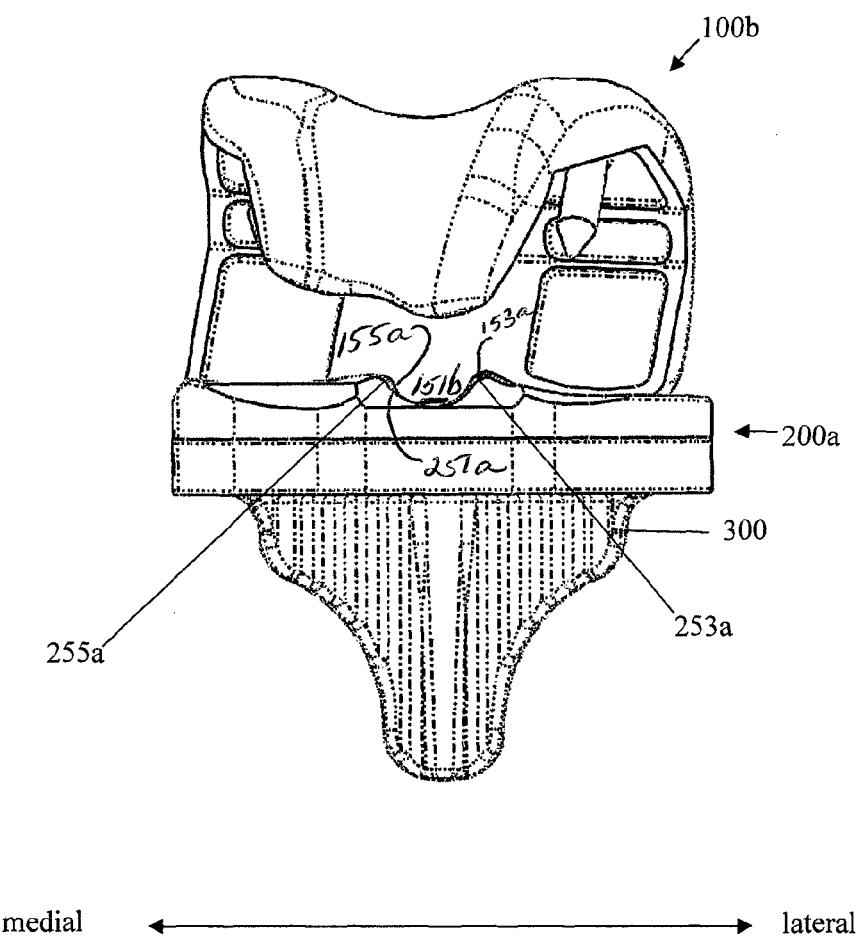
FIG. 8B is an assembled anterior-posterior view from the posterior of the femoral and tibial articular components of FIGS. 7B and 7C at approximately 130° of flexion.

FIGS. 8A and 8B help illustrate the interaction of the ridge 151b of the asymmetric embodiment with the groove 251a. Both FIGS. 8A and 8B are coronal plane views of the implant looking from the posterior direction. FIG. 8A shows the femoral and tibial articular components 100a and 200a at about 90° of knee flexion and FIG. 8B shows the femoral and tibial articular components 100a and 200a at about 155° of knee flexion.

At 80° flexion and less (see FIG. 8A), the side edges 153a, 155a of the ridge 151 are straight. The groove 251a is wider in the coronal direction than the ridge 151a, but, when implanted, is offset medially therefrom so that the lateral side edge 153a is substantially congruent with the lateral side wall 253a of the groove so that all of the extra space in the groove 251a is on the medial side. Thus, the tibial component can, but is not forced to, rotate about the longitudinal axis of the tibia relative to the femoral component. With reference now to FIG. 8B, at angles of knee flexion greater than 80°, the sloped portion of lateral side edge 153a starts to become congruent with the lateral side wall 253a of the groove 253 to create a wedging effect on the lateral side of the prosthesis, thereby forcing internal rotation of the tibial articular component 200a relative to the femoral articular component 100a as flexion increases past 90°. Also as seen in FIG. 8B, at higher knee flexion angles, the wider portion of the ridge fills up more of the groove (in the coronal dimension) thus also decreasing the possibility of lateral shearing of the ridge within the groove.

The interaction of the ridge 151a, or 151b and the groove 251a also can help facilitate rollback of the femoral articular component 100a, 100b on the tibial articular component 200a at deeper angles of flexion (i.e., rolling of the femoral articular component 100a, 100b posteriorly relative to the tibial articular component 200a). Specifically, remember that for knee flexion angles of 80° and greater, the lateral condylar articular surface 103a, 103b is getting smaller than the medial condylar articular surface 101a, 101b. Thus, the center of the force between the femoral and tibial articular components actually moves laterally as the knee increases flexion past 80°. Thus, to facilitate rollback, the mating ridge 151a or 151b and groove 251a are positioned so that they engage fully by about 80° of flexion. Thereafter, as flexion increases, the center of rotation of the femoral articular component 100a or 100b relative to the tibial articular component 200a transitions smoothly from the more stabilized medial compartment (i.e., the medial condylar articular surface 101a or 101b and the medial tibial articular surface 201a) to the ridge 151a or 151b and groove 251, which is more central to the overall knee in the medial-lateral direction.

According to one embodiment, ridge 151a, 151b and groove 251a are designed so that, at flexion angles of less than about 40° to 60°, the ridge 151a, 151b and groove 251a are not in contact so that rotation of the implant is guided by the interaction of the medial and lateral condylar articular surfaces with the medial and lateral tibial articular surfaces. However, some contact may occur with tibial internal or external rotation.

Then, as the ridge and groove engage at angles greater than 40° to 60° of knee flexion, the internal and external rotation of the tibia relative to the femur is restricted or guided by the contacting side edges 253a, 255a or 253b, 255b of the ridge with the side walls 253a, 255a of the groove.

Figure 9B:
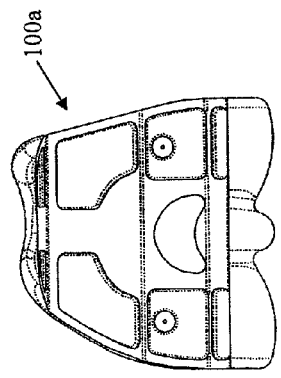
FIG. 9B is a coronal or medial-lateral cross sectional view of the femoral articular component of FIG. 7A taken through the centers of the distal condyles.
Figure 9A:
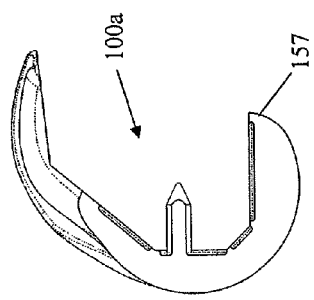
FIG. 9A is a sagittal cross sectional side view of the femoral articular component of FIG. 7A taken through section A-A of the medial condyle.
Figure 9D:
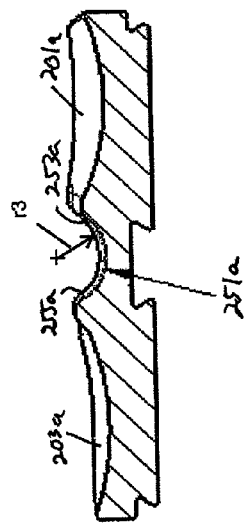
FIG. 9D is medial-lateral cross-sectional view of the tibial articular component of FIG. 7C taken through section B-B.
Figure 9C:
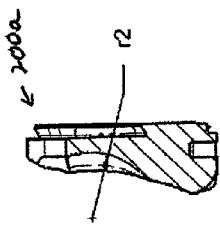
FIG. 9C is a sagittal cross sectional side view of the tibial articular component of FIG. 7C taken through section A-A.

FIGS. 9A and 9B are cross-sectional sagittal and coronal views, respectively, through the ridge 151a. FIGS. 9C and 9D are cross-sectional sagittal and coronal views, respectively through the groove 251a. With reference to FIGS. 9A and 9C, the sagittal radius of the ridge, r1, and the sagittal radius of the groove, r2, may be made identical or nearly identical to maximize congruency of the ridge 151a in the groove 251a and thereby minimize stresses. Likewise, with reference to FIGS. 9B and 9D, the coronal radius, r3, of the groove 251a (at least at and near the lateral and medial side walls 253a, 255a) also may be made identical or nearly identical to the coronal radius, r4, of the ridge 151a (again, at least at and near its side edges 153a, 155a or 153b, 155b) to maximize congruency.

The various features disclosed herein for a TKR implant maybe combined in other permutations than those expressly discussed herein. The features provide an implant that allows very high degrees of flexion, such as 155° or more, that allows, but does not force rotation of the tibia relative to the femur at lower angles of flexion, and then either allows or forces internal rotation of the tibia at higher degrees of flexion, thereby providing a much more natural acting prosthetic knee than conventional TKR prostheses.

It should be understood that, in some patients, it may be desirable to implant a TKR prosthesis in accordance with the principles of the present invention that omits the post and cam feature and/or ridge and groove feature so as not to force roll back in the knee or any of the other behaviors discussed herein above in association with such features.

Having thus described a few particular embodiments of the invention, various alterations, modifications, and improvements will readily occur to those skilled in the art. Such alterations, modifications, and improvements as are made obvious by this disclosure are intended to be part of this description though not expressly stated herein, and are intended to be within the spirit and scope of the invention. Accordingly, the foregoing description is by way of example only, and not limiting. The invention is limited only as defined in the following claims and equivalents thereto.

What is claimed is:

1. A prosthesis for replacement of at least part of a knee joint comprising:

a tibial articular component having a medial compartment defining a medial tibial articular surface, a lateral compartment defining a lateral tibial articular surface, and a first formation between the medial compartment and the lateral compartment; and a femoral articular component having a medial condylar articular surface for bearing on the medial tibial articular surface, a lateral condylar articular surface for bearing on the lateral tibial articular surface, and a second formation between the lateral condylar articular surface and the medial condylar articular surface for bearing on the first formation of the tibial articular component;

wherein at least one of the first and second formations is partially symmetric and partially asymmetric such that the interaction of the first and second formations during articulation of the femoral articular component relative to the tibial articular component does not bias any rotation of the tibial articular component relative to the femoral articular component at relative orientations corresponding to knee flexion of less than 60° of knee flexion and the interaction of the femoral and tibial formations during articulation of the femoral articular component relative to the tibial articular component biases internal rotation of the tibial articular component relative to the femoral articular component at relative orientations corresponding to knee flexion of greater than 110° of knee flexion, and wherein the first formation is a groove longitudinally oriented in a sagittal direction and the second formation is a ridge and wherein the ridge is positioned to slide in the groove in the anterior-posterior direction.

2. The prosthesis of claim 1 wherein the asymmetry comprises a widening of the ridge in a lateral direction, the asymmetry located such that it is congruent with the groove at angular orientations of the femoral articular component relative to the tibial articular component corresponding to angles of greater than 110° of knee flexion and is not congruent with the groove at angular orientations of the femoral articular component relative to the tibial articular component corresponding to angles of less than 80° of knee flexion.

3. The prosthesis of claim 1 wherein the groove comprises a lateral side wall and a medial side wall and the asymmetry comprises a medial curvature of the lateral side wall in an anterior to posterior direction, the asymmetry configured such that it is congruent with the ridge at angular orientations of the femoral articular component relative to the tibial articular component corresponding to angles of greater than 110° of knee flexion and is not congruent with the ridge at angular orientations of the femoral articular component relative to the tibial articular component corresponding to angles of less than 80° of knee flexion.

4. The prosthesis of claim 1 wherein the groove is wider in the medial-lateral direction than the ridge.

5. The prosthesis of claim 1 wherein the groove is offset medially relative to the ridge so that the ridge occupies more of the lateral side of the groove than the medial side of the groove.

* * * * *